United States Patent [19]

Friedman et al.

[11] Patent Number: 5,547,877
[45] Date of Patent: Aug. 20, 1996

[54] METHODS FOR THE RAPID DETECTION OF TOXIC HALOGENATED HYDROCARBONS AND KITS USEFUL IN PERFORMING THE SAME

[75] Inventors: Stephen B. Friedman, Chapel Hill; William B. Studabaker; Patrick D. Mize, both of Durham, all of N.C.

[73] Assignee: Ensys Environmental Products, Inc., Research Triangle Park, N.C.

[21] Appl. No.: 329,097

[22] Filed: Oct. 25, 1994

[51] Int. Cl.⁶ .................................................. G01N 21/25
[52] U.S. Cl. .......................... 436/126; 436/124; 436/125; 436/178; 422/68.1; 422/69; 422/59
[58] Field of Search ..................................... 436/172, 124, 436/125, 178, 126; 422/61, 69, 70, 68.1, 59, 60

[56] References Cited

U.S. PATENT DOCUMENTS

| | | |
|---|---|---|
| 4,666,672 | 5/1987 | Miller et al. . |
| 4,929,562 | 5/1990 | Anderson et al. . |
| 5,094,817 | 3/1992 | Aoki et al. . |
| 5,273,909 | 12/1993 | Piasio . |
| 5,358,875 | 10/1994 | Goswami ......................... 436/124 |

OTHER PUBLICATIONS

Fujiwara Reaction and Determination of Carbon Tetrachloride, Chloroform, Tetrachloroethane, and Trichloroethylene in Air, vol. 38, No. 11, Oct. 1966, pp. 1532–1536.

Multicomponent Determination of Chlorinated Hydrocarbons Using a Reaction–Based Chemical Sensor. 1. Multivariate Calibration of Fujiwara Reaction Products, Analytical Chemistry, vol. 66, No. 20, Oct. 15, 1994, pp. 3328–3336.

Multicomponent Determination of Chlorinated Hydrocarbons Using a Reaction–Based Chemical Sensor. 2. Chemical Speciation Using Multivariate Curve Resolution, Analytical Chemistry, vol. 66, No. 20, Oct. 15, 1994, pp. 3337–3344.

Multicomponent Determination of Chlorinated Hydrocarbons Using a Reaction–Based Chemical Sensor. 3. Medium–Rank Second–Order Calibration with Restricted Turcker Models, Analytical Chemistry, vol. 66, No. 20, Oct. 15, 1994, pp. 3345–3351.

A Simple Spectrophotometric Method for the Determination of THMs in Drinking Water, by David A. Reckhow and Pamela D. Pierce, AWWA Research Roundation and American Water Works Association.

Mueller et al., Amer. Lab., (1974),6(5), 49.

Angel, S. M. et al., Quarterly Technical Report; Jun. 18, 1987, Lawrence Livermore Nat. Lab.

Primary Examiner—Lyle A. Alexander
Attorney, Agent, or Firm—Oblon, Spivak, McClelland, Maier, & Neustadt, P.C.

[57] ABSTRACT

Methods for the detection, identification and/or quantitation of halogenated hydrocarbons in aqueous samples and kits for performing the methods are provided which provide high sensitivity and can provide high selectively for individual halogenated hydrocarbons such as TCE or THMs. An additional method is provided for the sensitive determination of TTHM in an aqueous sample. These methods use a general two step procedure of (1) extracting and concentrating the halogenated hydrocarbons from the aqueous sample and (2) subjecting the concentrated halogenated hydrocarbons to a modified Fujiwara reaction to provide chromophoric products which can be analyzed by absorption spectra of the resulting mixtures.

15 Claims, 11 Drawing Sheets

WAVELENGTH, nm

WAVELENGTH, nm

WAVELENGTH, nm

WAVELENGTH, nm

METHODS FOR THE RAPID DETECTION OF TOXIC HALOGENATED HYDROCARBONS AND KITS USEFUL IN PERFORMING THE SAME

BACKGROUND OF THE INVENTION

1. Field of the Invention

The present invention relates to methods for the rapid, sensitive detection of toxic halogenated hydrocarbons based, in part, on use of a modified Fujiwara reaction, and kits for performing the methods.

2. Discussion of the Background

Nearly all municipal water systems throughout the United States disinfect the public water supply through the addition of halogenating agents. However, while these agents kill various microorganisms in the water supply, they unfortunately also result in the production of various halogenated byproducts such as trihalomethanes (THMs).

THMs are a class of four compounds (i.e. chloroform, bromoform, dichlorobromomethane, and dibromochloromethane). These THMs are pathogenic and regulatory limits have been placed on their presence in water. A detection method for THMs must have sensitivity for the four compounds, alone or in combination, at a concentration in the parts per billion, and must demonstrate comparable recognition of the four THM compounds to minimize a bias in the interpretation of samples that may contain individual THMs or mixtures of the compounds.

The literature describes various methods for the measurement of organic halides from aqueous solution. In one method the aqueous solution of organic halide is passed through a packed column of granular activated carbon (GAC). Organic halides are strongly adsorbed and are completely removed from solution. The GAC, with adsorbed organic halide, is burned and total organic halide is determined by mircocoulometric titration. This comprises EPA Methods 9020, Total Organic Halides (TOX).

Organohalogen compounds such as TCE or the THMs, react with pyridine in the presence of base in a process conventionally known as the Fujiwara reaction.

Classical Fujiwara methods were developed for the detection of organohalogens in pyridine, where pyridine was used either as the extraction solvent for biological materials, or as the impinging solvent for air sampling. But classical Fujiwara chemistry, while well documented, has not been thought compatible with the sensitivity and response normalization requirements necessary for use as an effective assay of total THMs (TTHM). The chemistry does not have the prerequisite sensitivity and the sensitivity to each of the four THMs in the population is different. A test method for the determination of TTHM would thus have limited efficacy using the Fujiwara chemistry currently in the literature.

Lugg (Anal. Chem., 1966, 38, 1532) described the optimization of a homogeneous Fujiwara reaction. However, Lugg's method cannot be used to provide an accurate sensitive test for TTHM for the following reasons:

(1) Lugg's reaction is optimized for sensitivity to a single compound such as chloroform. The kinetics of the reaction of chloroform are considerably different than those for the other trihalomethanes, and the proper selection of reaction time is critical to ensuring normalized response.

(2) Lugg uses sodium hydroxide as the base in the Fujiwara reaction. However, the use of metal hydroxides results in turbid reaction mixtures, most likely as a result of formation of insoluble metal halides as a reaction byproduct. Thus, the sample absorbance cannot be measured accurately under such conditions.

Miller et al. U.S. Pat. No. 4,666,672 refers to the fluorometric detection of halogenated hydrocarbons using the Fujiwara reaction in a two phase system (pyridine or nicotinamide with an aqueous hydroxide). In particular, an optrode which detects halogenated hydrocarbons is shown. The difficulties of quantifying the presence of halogenated hydrocarbons by the Fujiwara reaction are discussed.

Anderson, deceased et al, U. S. Pat. No. 4,929,562 pertains to a method and optrode for detecting gem halogenated hydrocarbons based on a single phase Fujiwara reaction which uses a hindered nitrogen base. Pyridine is used in an amount of from 60–96% by volume based on the volume of the aqueous solution which contains the hindered nitrogen base. It is also stated that the absorption bands depend upon the reactants and hydrocarbon present. However, the dependence of the reaction products absorbance on the concentration of water is not addressed.

In order for an assay for total THM to be useful, the response of the assay must be normalized to provide equivalent detection of each member of the THMs on a weight basis. However, the normalization of THM response is difficult to achieve. Reasons for this include that (1) the THMs vary in molecular weight by more than twofold (chloroform=119, bromoform=253), giving twice the number of chloroform molecules on a per weight basis; (2) they vary in halogen type and stoichiometry and (3) the kinetics of formation of the Fujiwara reaction product varies among the compounds, causing differences in the chromogenic response of the Fujiwara reaction product. Thus on a weight basis, any assay reaction product of chloroform would be expected to generate more than twice the signal produced by the same weight of bromoform.

SUMMARY OF THE INVENTION

Accordingly, one object of the present invention is to provide a method for the detection of halogenated hydrocarbons having high sensitivity for TCE and/or THMs.

A further object of the present invention is to provide a method for the detection of total trihalomethanes (TTHM) having high sensitivity and which minimizes bias for any single THM compound.

A further object of the present invention is to provide a method for the measurement of TTHM which normalizes the response for each of the different THM compounds using a modified Fujiwara reaction.

A further object of the present invention is to provide a kit for performing the concentration and Fujiwara type reaction steps of the present methods, which kit is readily used in laboratory and field settings.

These and other objects of the present invention have been satisfied by the discovery of a method for the selective, sensitive detection of total trihalomethanes (TTHM), in an aqueous sample comprising:

a) contacting said aqueous sample with a solid phase extraction medium to essentially quantitatively adsorb trihalomethanes (THMs) from said aqueous sample;

b) eluting the adsorbed THMs from said solid phase extraction medium with pyridine to essentially quantitatively remove THMs from the solid phase extraction medium;

c) contacting the thus formed pyridine solution of eluted THMs with 0.1±0.25% of a base reagent and an amount of water to form a chromophoric product from each THM, wherein said amounts of base and water are sufficient to provide an optical absorption response for each chromophoric product which is approximately equal on a weight/weight basis to an optical absorption response for each of the chromophoric products formed from the other THMs; and d) determining a concentration of TTHM by measuring an absorption spectrum for the product of step c).

In a broader sense the present invention provides a method for detecting the presence of one or more halogenated hydrocarbons in an aqueous sample suspected of containing the same, comprising:

a) contacting said aqueous sample with a solid phase extraction medium, to adsorb said one or more halogenated hydrocarbons, if present, from said aqueous sample;

b) eluting the adsorbed halogenated hydrocarbons from said solid phase extraction medium with an organic solvent capable of essentially quantitative removal of halogenated hydrocarbons from the solid phase extraction medium;

c) contacting, independently, a plurality of aliquots of the eluted halogenated hydrocarbons with pyridine, a base, and from 0–18% by volume of water, wherein each aliquot is contacted with a volume of water different from all other aliquots;

d) determining the presence, identity or concentration, or a combination thereof, of each halogenated hydrocarbon in the aqueous sample based on a set of kinetic absorbance spectra obtained by measuring absorbance of each aliquot at a time, t, after said contacting step c).

Also described by the present invention are kits for carrying out these assays.

BRIEF DESCRIPTION OF THE DRAWINGS

A more complete appreciation of the invention, and many of the attendant advantages thereof, will be readily obtained as the same becomes better understood by reference to the following detailed description when considered in connection with the accompanying drawings, wherein.

DESCRIPTION OF THE PREFERRED EMBODIMENTS

Figure 1:
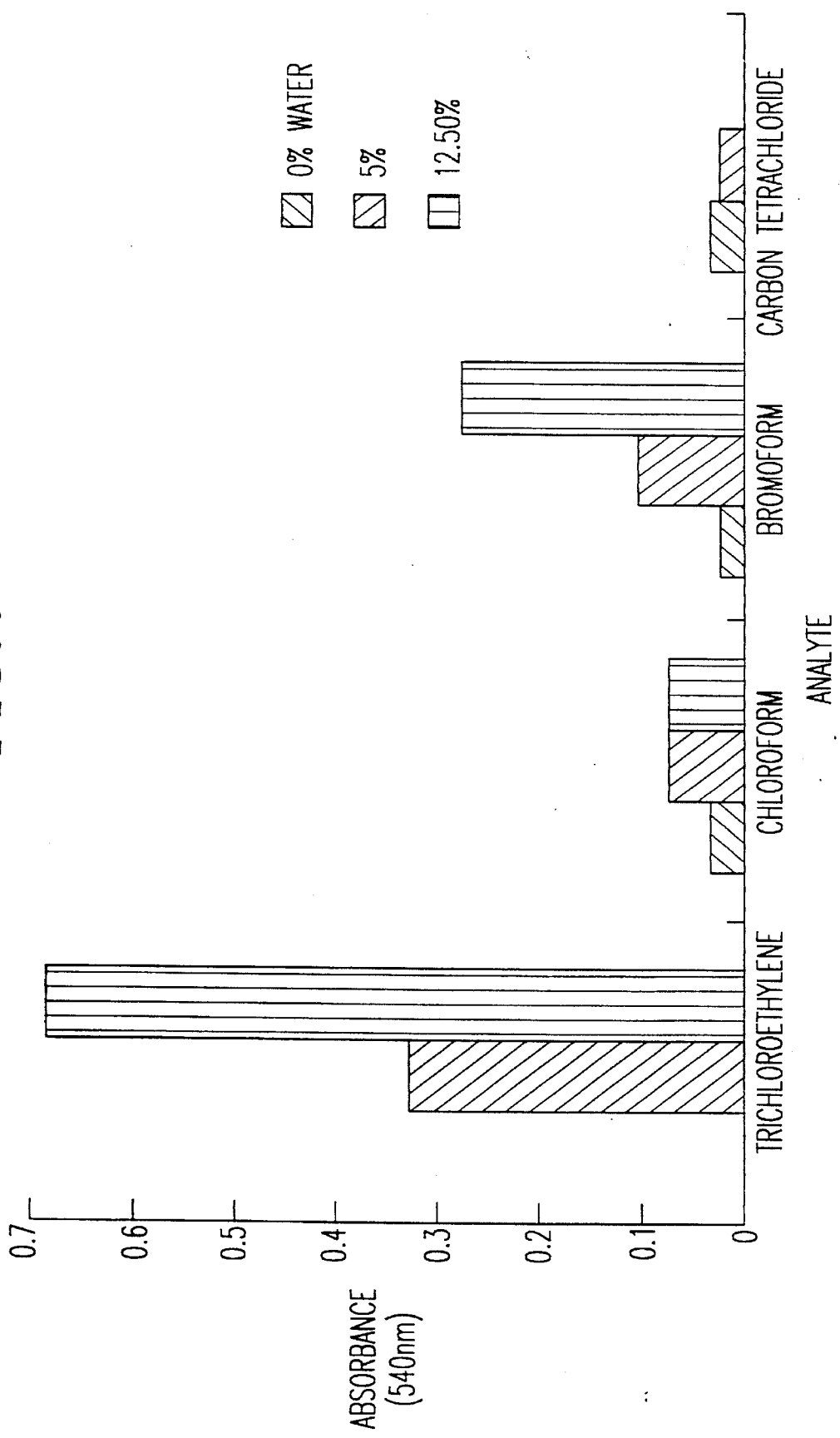
FIG. 1 shows the relative absorbance profiles of various halogenated hydrocarbons after 10 min of color development.

The present invention relates to methods for the detection of halogenated hydrocarbons (i.e., toxic halogenated solvents) in an aqueous solution. The method uses two steps; (1) concentration of a halogenated hydrocarbon present in an aqueous solution, (2) detection of the concentrated halogenated hydrocarbon by a Fujiwara type reaction. Step (1) is accomplished by adsorbing the halogenated hydrocarbon present in the aqueous solution onto a solid phase extraction (SPE) column. The adsorbed halogenated hydrocarbon is then eluted with a solvent capable of near quantitative desorption of the halogenated hydrocarbon from the SPE column. Step (2) involves treating the concentrated sample with pyridine (which may already be present) and a base in the presence of a specific amount of water.

The various embodiments of the present methods take advantage of a property of the product of a Fujiwara reaction which the present inventors were the first to discover. In particular, the present inventors have discovered that each of the Fujiwara reaction products prepared by reaction of the various halogenated hydrocarbons with pyridine result in unique absorbance patterns when differing amounts of water are present in the reaction medium. From this discovery, the present inventors have developed a series of methods for the selective detection of trichloroethylene (TCE) and methods for the simultaneous and selective detection of the various halogenated hydrocarbons based upon the characteristic absorbance patterns displayed.

However, prior to discussing the details of the Fujiwara reaction as used in the present invention, it is necessary to first provide a method for obtaining a sample which is suitable for use in a Fujiwara reaction scheme. Water samples to be tested may contain only minute amounts of the halogenated hydrocarbons. However, due to regulatory requirements it is necessary to have a method which can detect and identify these minute quantities, and in the case of THMs detect the individual compounds, alone or in combination. The classical Fujiwara reaction cannot achieve this kind of sensitivity. Thus, the methods of the present invention each use an initial sample processing step which results in the concentration of the halogenated hydrocarbon(s) present in an aqueous sample to provide a concentrated sample suitable for the Fujiwara type reaction.

This initial sample processing step accounts for much of the sensitivity of the present methods. As noted previously, granular activated carbon (GAC) is known to adsorb an aqueous solution of organic halides. The granular activated carbon has strong adsorption for organic halides and can remove them completely from the aqueous solution. This particular feature of granular activated carbons is taken advantage of in EPA methods 9020, for Total Organic Halides (TOX) as described previously. However, in order to use an extraction technique to obtain a concentrated sample for use in the Fujiwara type reaction, it is necessary to have a solid phase extraction medium which has high affinity and relative flow-rate insensitivity for the organic halides in aqueous solution but from which the organic halides can be readily removed with the appropriate choice of solvent. Several hurdles must be overcome in this regard. First, conventional procedures for the removal of analytes from water using a solid phase extraction technique use vacuum filtration, which risk the volatilization of volatile analytes present in the water, such as the THMs. Second, while normal solid phase extraction materials do not typically extract THMs from water with any efficiency, even those active carbons which do show ability to extract the THMs have shown significant variability in the analyte absorption. A third obstacle is that there is no guidance in the literature to suggest an appropriate solvent for near quantitative elution of the organic halides from carbons or other SPE materials. Fourth, the solvent selected should be ultimately compatible with the Fujiwara detection chemistry and thus should not introduce a decrease in sensitivity by dilution of the sample.

The ability to nearly quantitatively elute the adsorbed organic halides from the SPE medium using a Fujiwara-compatible solvent would allow detection and quantitation of the individual organic halides at regulatory prerequisite concentrations. Suitable SPE media for use in the present methods include granular activated carbons (GACs), $C_6$–$C_8$ modified silica columns, and clathrating agents such as cyclodextrins and crown ethers.

One key to the success of the present methods is the ability to achieve near quantitative elution of the adsorbed halogenated hydrocarbons from the SPE material. Poor elution of a organo halide, like TCE, from GAC is seen with organic solvents such as isooctane. The present inventors have found that the adsorbed halogenated hydrocarbon can be recovered from GAC nearly quantitatively by the use of aromatic amine solvents such as pyridine, the picolines (methyl pyridines), the lutidines (dimethyl pyridines) and other pyridines substituted by substituents compatible with and inert to the Fujiwara reaction conditions. Alternatively, acetonitrile can be used for the elution step.

As an example, when large amounts of a dilute aqueous solution of a halogenated hydrocarbon (1 liter) are passed through a small amount of GAC (100 mg) at up to 200 ml/min, the halogenated hydrocarbon is adsorbed nearly quantitatively. The adsorbed halogenated hydrocarbon then can be removed nearly quantitatively from the GAC with a small amount of pyridine. If the amount of pyridine used is 1.0 mL, the adsorption/extraction step results in concentration of halogenated hydrocarbon by a factor of approximately 1000. Use of pyridine is particularly advantageous for the detection of organohalides, since pyridine is the solvent and reactant of choice for the Fujiwara reaction of step (2) of the present invention.

To achieve the required regulatory sensitivity in the detection of THMs, a GAC capture device is used to capture and concentrate the THMs from a water sample. This device can be configured either as a GAC impregnated filter (such as Empore™, sold by 3M Corp.) in a plastic housing containing two connection tube connecting fittings (e.g. luer lock), or as an in-line mini-GAC column similarly configured to contain fittings. These filters can be placed at the end of a syringe containing the water sample, or in-line with plastic tubing that supplies the sample by means of a peristaltic pump.

In an additional embodiment of adsorption column, the SPE material can be placed in a cylindrical column equipped with fittings capable of coupling to a pressurized water source, such as a domestic water faucet. Such a column could then be filled and capped by a consumer, and sent to a laboratory for analysis, in order to test their home water supply for toxic halogenated hydrocarbons.

The capture efficiency for THMs by these devices has been observed to be essentially flow rate independent up to a sample velocity of 200 ml/minute. Thus, by increasing the sample volume, the amount of captured THMs is increased, and proportionally so is the sensitivity of the present method. This method provides a mechanism to not only obtain the prerequisite sensitivity needed to produce a chromogenic response from the Fujiwara chemistry of step (2), but also a way to respond to the increase in sensitivity that is anticipated to meet future regulatory requirements.

Once THMs are captured on the GAC sorbent, near total elution of the THMs can be achieved using the same eluting solvents noted above, with pyridine being preferred as the eluting solvent. Conveniently, the use of pyridine as the eluting solvent allows direct integration of the sample processing (concentration) component and the Fujiwara-based detection component. The sample can be collected on the capture device, connected to a syringe containing either pyridine, or a mixture of pyridine and the base used in the Fujiwara reaction, and eluted into a reaction vessel.

Once the concentrated sample is obtained, the second step of the present method, a Fujiwara type chromogenic reaction can be performed. Several factors modify and increase the selectivity and kinetics of the Fujiwara reaction between a pyridine compound and an organohalide. These factors include, but are not limited to, water content, reaction temperature, the base used and the base concentration. The amount of water and base present in the reaction mixture profoundly affects the formation and stability of chromophores which are characteristic for each of the particular organohalides.

As the pyridine compound to be used in the Fujiwara reaction, one can use pyridine or $C_1$–$C_4$ alkyl substituted pyridines. Also suitable for the pyridine compound are soluble solid compounds which contain pyridine moeities, such as pyridine based dyes or terpyridyl compounds, and pyridine containing polymers either in solution or in the solid phase. These soluble solid compounds containing pyridine moeities and pyridine containing polymers are especially suitable for use in the Fujiwara reaction when the above described elution step has been performed with a non-pyridine based solvent. However for optimum sensitivity and ease of performance, pyridine is preferred as both the elution solvent and the Fujiwara reactant/solvent.

Although the literature desribes that many organo halides can be detected with varying sensitivities using the Fujiwara reaction, the fact that the utility of the Fujiwara reaction can be increased by controlling the base reagent and water content has not been realized until now.

In a first embodiment of the present invention, a sample containing halogenated hydrocarbon is subjected to a Fujiwara reaction at a plurality of different water concentrations, preferably three different concentrations, most preferably at 0%, 3–5% and 12.5% water. The absorbance spectrum produced at each water concentration is then measured. Due to the fact that the Fujiwara reaction product of each halogenated hydrocarbon has a different $A_{max}$ at 540 nm (with the maximum absorbance being at 538 nm) and different kinetics in producing absorbance depending on the amount of water present, during the reaction one can then deconvolute the series of spectra obtained and determine the presence and concentration of each halogenated hydrocarbon. Each compound produces a unique response signature over time when analyzed at different water concentrations. FIG. 1 shows the relative absorbance profiles of various halogenated hydrocarbons after 10 min of color development. In the presence of different water and base concentrations, a given halogenated hydrocarbon will produce different chromophores. Each distinct chromophore may have a unique extinction coefficient, $\lambda_{max}$, and rate of production under the Fujiwara conditions. Because of these unique absorbance signatures for the various halogenated hydrocarbons, it is thus possible to use the plural absorbance spectra provided by the reaction products of the Fujiwara reaction at the various water concentrations to detect and identify the presence of the halogenated hydrocarbons.

While the pathways for the production of the different chromophores from each of the different halogenated hydrocarbons are unknown as are the identities of the various chromophores, the present inventors hypothesize that the amount of water and/or base in the Fujiwara reaction have profound effects on the ability of side reactions to take place during the Fujiwara procedure. However, the present inventors do not wish to be bound to this hypothesis, as it is only one possible explanation for the reaction products and data observed.

In performing this first embodiment of the present invention, the sample to be tested is split into a plurality of assay portions (preferably 3). These plurality of assay portions are then each subjected to the extraction/concentration protocol set forth above, using pyridine as the eluent from the SPE material. Each pyridine and sample eluate is collected into a tube containing a specific amount of water, with each tube containing a different amount of water than the others. Base is then added to each tube. Alternatively, the base can be added to the pyridine elution solvent prior to elution. In a further embodiment, the water, base or pyridine or a mixture of two or more of these can be used as the elution solvent. When the water or base are present at the desired levels in the elution solvent initially, there is no need to add additional water or base after elution of the halogenated hydrocarbons from the SPE material. Additionally, the SPE material often retains a set amount of water, depending on the SPE material and size of the column (if a column is used). Thus since the amount of residual water contained in the SPE material after adsorption can be readily determined, this amount of water should be taken into account when determining the percentage of water in the assay sample after elution. The various water concentrations can vary from 0% to 18%, with one of the water concentrations preferably at 0%. The remaining water concentrations are preferred to be spread throughout the range of 0–18%. A preferred embodiment would use pyridine having water and base present in increments from 0–15%, with a most preferred embodiment using 3 tubes containing 0%, 3–5% and 12.5% water.

Upon elution of each assay portion into a separate vial using the desired pyridine/water combination, each of the eluted assay portions is analyzed kinetically using a photometer. The resulting set of absorbance spectra is then analyzed by computer to determine the concentration and type of the halogenated compound(s) present in the original sample. This analysis is performed based on the unique spectral characteristics of each of the THM and TCE compounds at the various concentrations of water. Each of these unique spectral "fingerprints" is stored in the computer for comparison against the spectra obtained during the assay. By spectral deconvolution of the set of spectra obtained in the assay, based on the stored standard spectra, the composition and concentration of the contituents in the original sample can be determined.

As an example, the present inventors have found that when no water is present in pyridine (1.0 mL) and 10 uL of a 40% aqueous solution of tetrabutylammonium hydroxide, TBAH, is used, TCE yields no chromophore at 540 nm after 1 hour of reaction. With 12.5% aqueous pyridine a strong transient absorption is seen at 540 nm which reaches maximum intensity at approximately 15 minutes. With $CCl_4$ (carbon tetrachloride) marked absorbance at 415 nm is observed with no water present and no absorbance is seen with 12.5% water. By contrast, $CHCl_3$ yields a strong stable absorbance at 475 nm with 5% aqueous pyridine and a strong stable absorbance at 540 nm with 12.5% aqueous pyridine.

In fact, in one embodiment of the present invention, by using small amounts of TBAH as the base and having a water content of 12.5% by weight, a very specific Fujiwara-type test can be developed for TCE. By using a water concentration of 0 or 5%, however, the response of TCE can be diminished or suppressed and the responses for THMs or carbon tetrachloride can be enhanced. Since each of the trihalomethanes (chloroform, bromoform, dibromochloromethane, and dichlorobromomethane) give a unique absorbance pattern at certain aqueous pyridine concentrations this method provides an assay for identifying and quantitating individual halogenated hydrocarbon compounds. When supplied with the spectral data obtained at the plurality of water concentrations, preferably 3, a computer program can deconvolute the spectra obtained and determine the type and concentrations of the THM or TCE present based upon the unique absorbance fingerprints of each compound. While the deconvolution of multiple spectra by computer is conventional, the present inventors were the first to realize that the amount of water present, the base used, the base concentration and the temperature used in the Fujiwara reaction can affect the chromophore formed during the Fujiwara reaction. These effects can be seen upon observation of the absorbance spectra produced at various wavelengths and reaction times.

In an alternative embodiment of the present invention, a method for the determination of total THM (TTHM) concentration is provided. In order for such a method to be viable, the method must be able to eliminate or at least minimize any bias created by testing samples containing the different THM compounds. Response normalization for the THM compounds was obtained by modifying the classic Fujiwara chemistry. The Fujiwara reaction produces a detectable chromophore when the THMs are exposed to a solution of pyridine and base. However, the chromogenic response of the different THMs varies by a factor of 4 using conventional Fujiwara chemistry.

Figure 2:
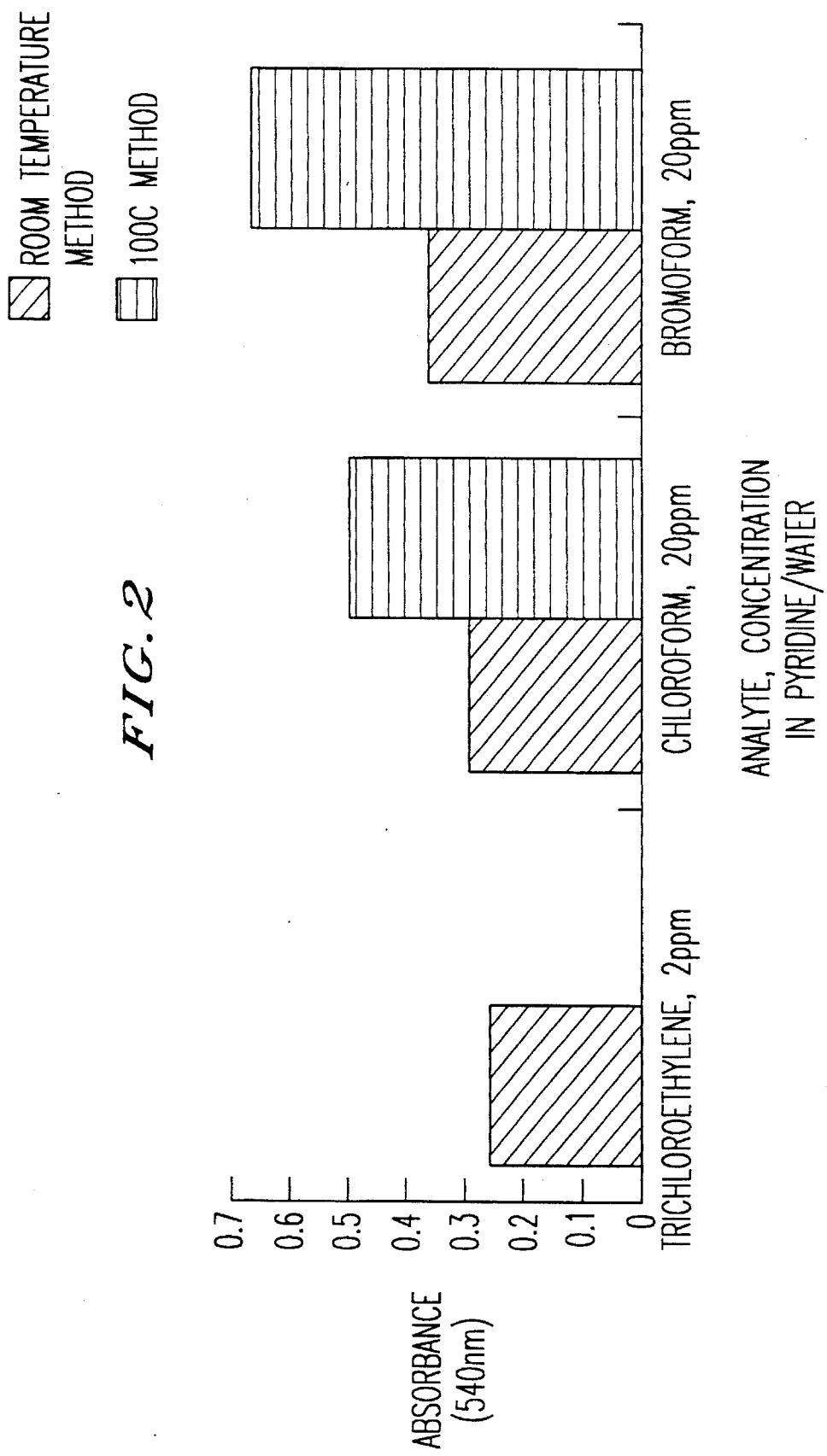
FIG. 2 graphically illustrates the effect of temperature and base concentration on the Fujiwara reaction of TCE and two trihalomethanes.

The present inventors have observed that the recognition of the THMs using Fujiwara chemistry can be influenced by controlling the chromophore produced, by manipulating the water and base content of the pyridine chemistry, and the temperature and time of the chromogenic reaction. Contrary to the observations reported by Lugg discussed (supra), the present inventors have found that increasing water concentration does not unambiguously reduce sensitivity. It actually increases the sensitivity when measured at certain time points but also increases the rate of decomposition so that the observed sensitivity and THM response produced depends upon the formation/decomposition ratio of the chromophore at a given time. At sufficiently high water concentrations the rate of decomposition supercedes the formation rate and thereby begins to decrease the attainable sensitivity at any time point. THM analytes form different colored products at different rates depending on the water and base content of the Fujiwara reaction, and those products also decompose at different rates. As a result, manipulating the reaction time, water, base and temperature at which the Fujiwara reaction is carried out confers addition control over selectivity. FIG. 2 illustrates this effect for TCE and two trihalomethanes.

Figure 3:
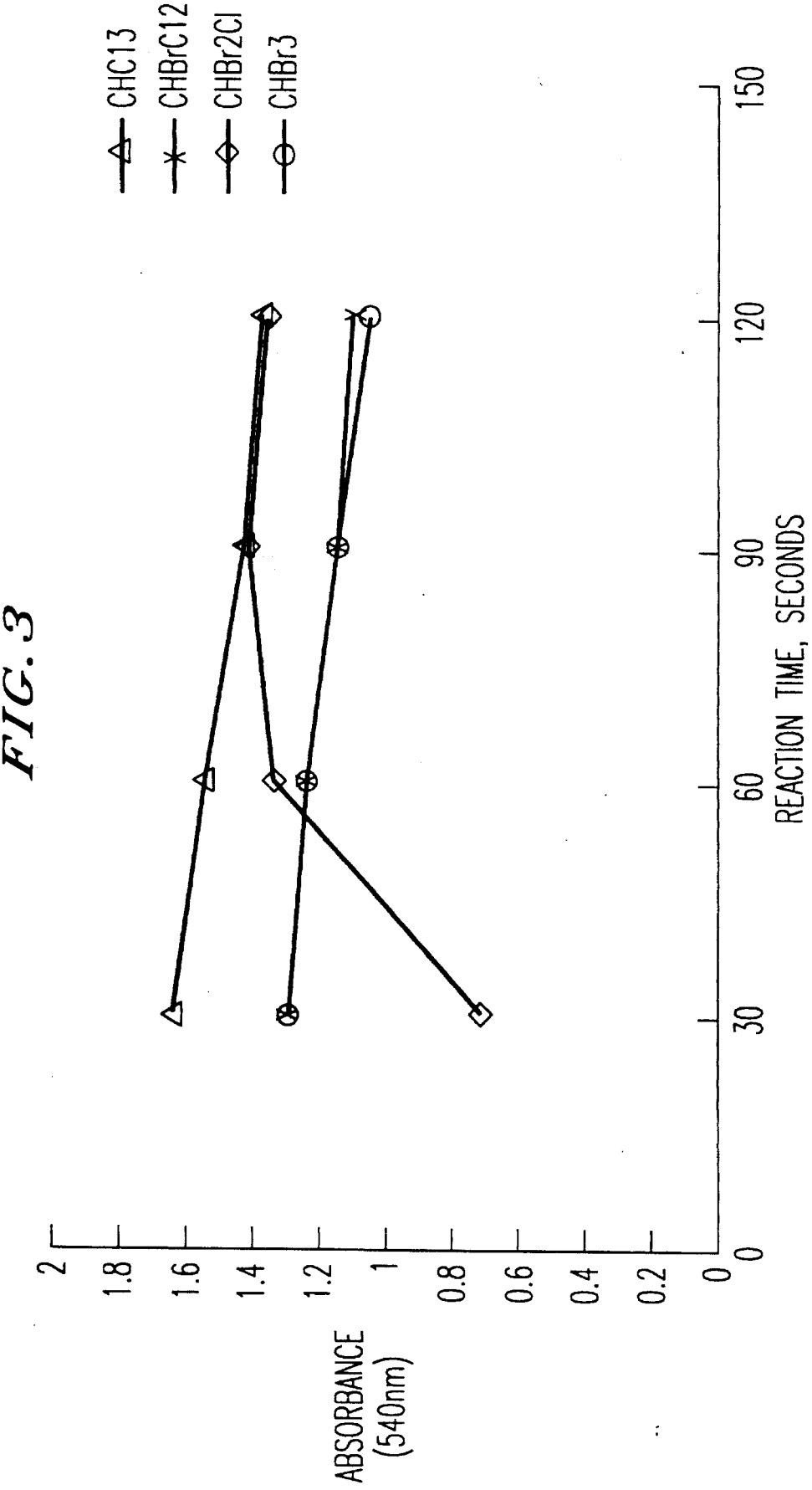
FIG. 3 graphically illustrates that maximum sensitivity is obtained by monitoring the absorbance at the point having the highest chromophore formation/decomposition ratio.

The rate of color formation of chloroform as determined at 540 nm is slower than for the other trihalomethanes of interest at water concentrations above 10%. In addition, the Fujiwara reaction product, thus the color being measured, is not stable at higher temperatures. FIG. 3 illustrates that maximum sensitivity is obtained by monitoring the absorbance at the point having a chromophore formation/decomposition ratio equal to 1. Suitable reaction times for the method of the present invention are in the range of 0.5 to 10 min while boiling at 100° C. or 30 to 300 min at room temperature (25° C.).

Figure 4:
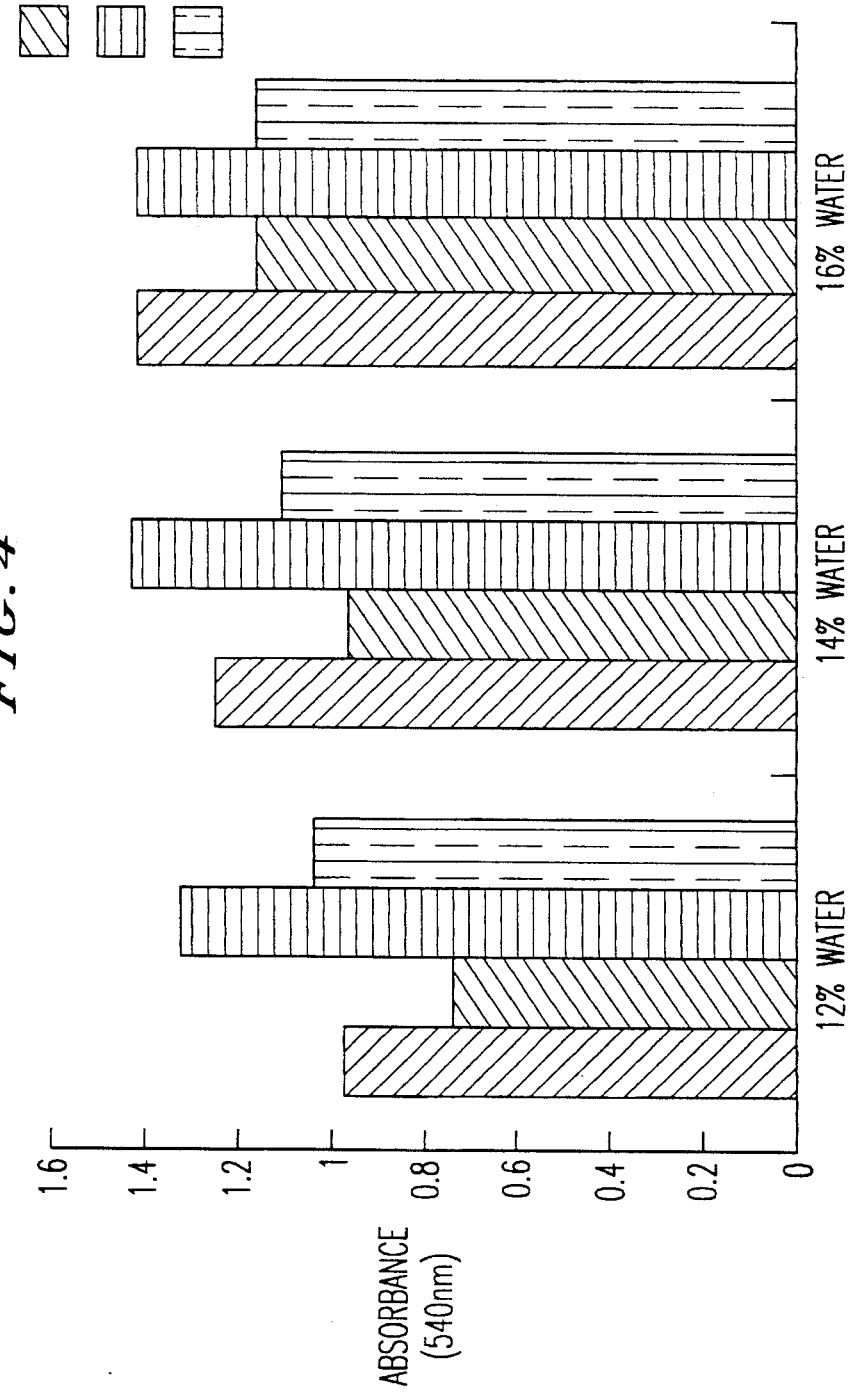
FIGS. 4 and 5 graphically illustrate how the water and base concentrations in the Fujiwara reaction, respectively, can be manipulated to modify the sensitivity of the Fujiwara reaction and the recognition of the four trihalomethanes.
Figure 5:
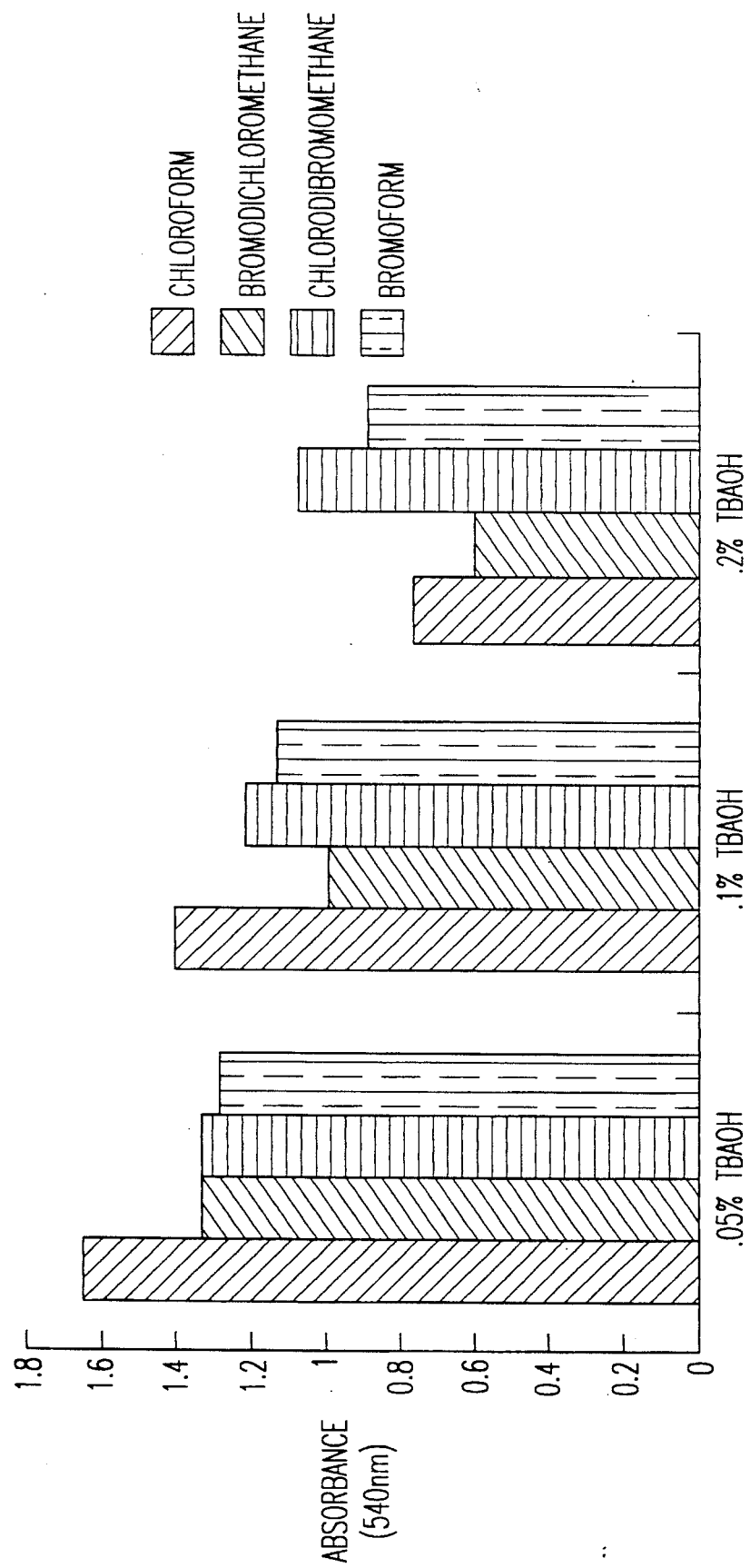
Figure 6A:
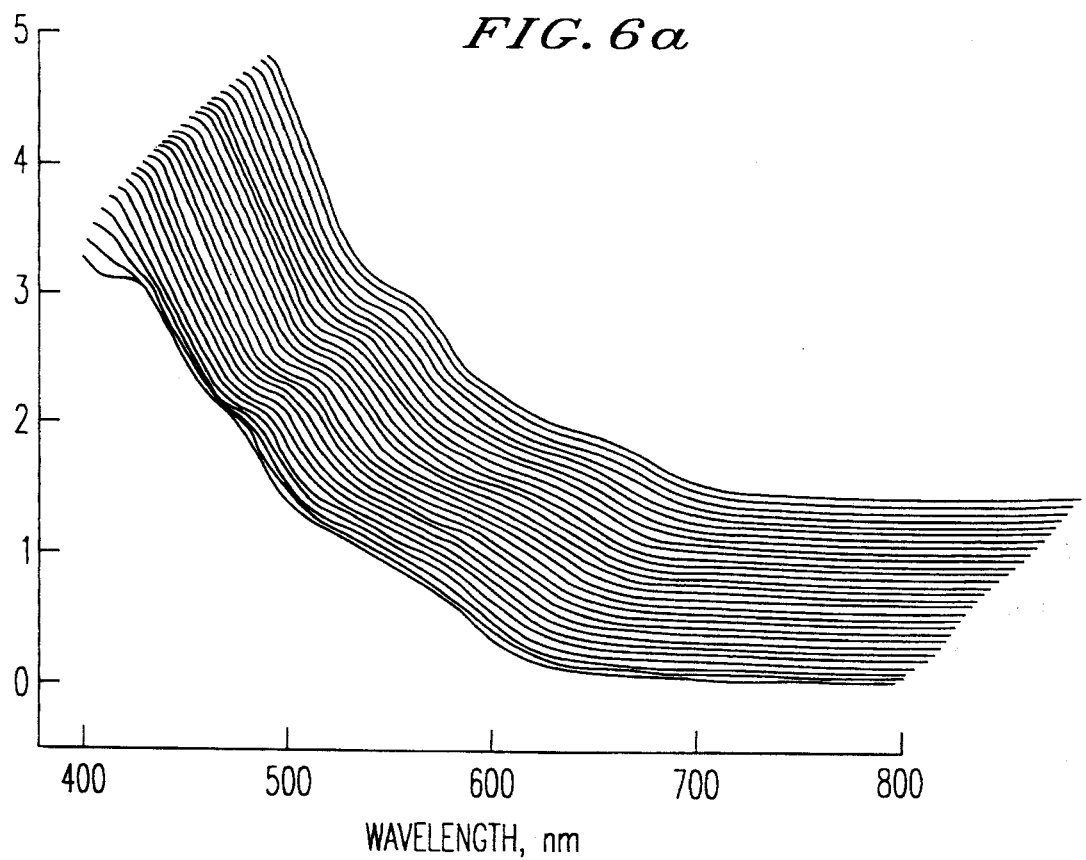
FIGS. 6(a–c), 7(a–c), 8(a–c) and 9(a–c) show the progressive change in the spectra of each of the THMs when the water concentration is changed from 0% (FIGS. 6(a), 7(a), 8(a) and 9(a)) to 5% (FIGS. 6(b), 7(b), 8(b) and 9(b)) and up to 12.5% (FIGS. 6(c), 7(c), 8(c) and 9(c)).
Figure 6B:
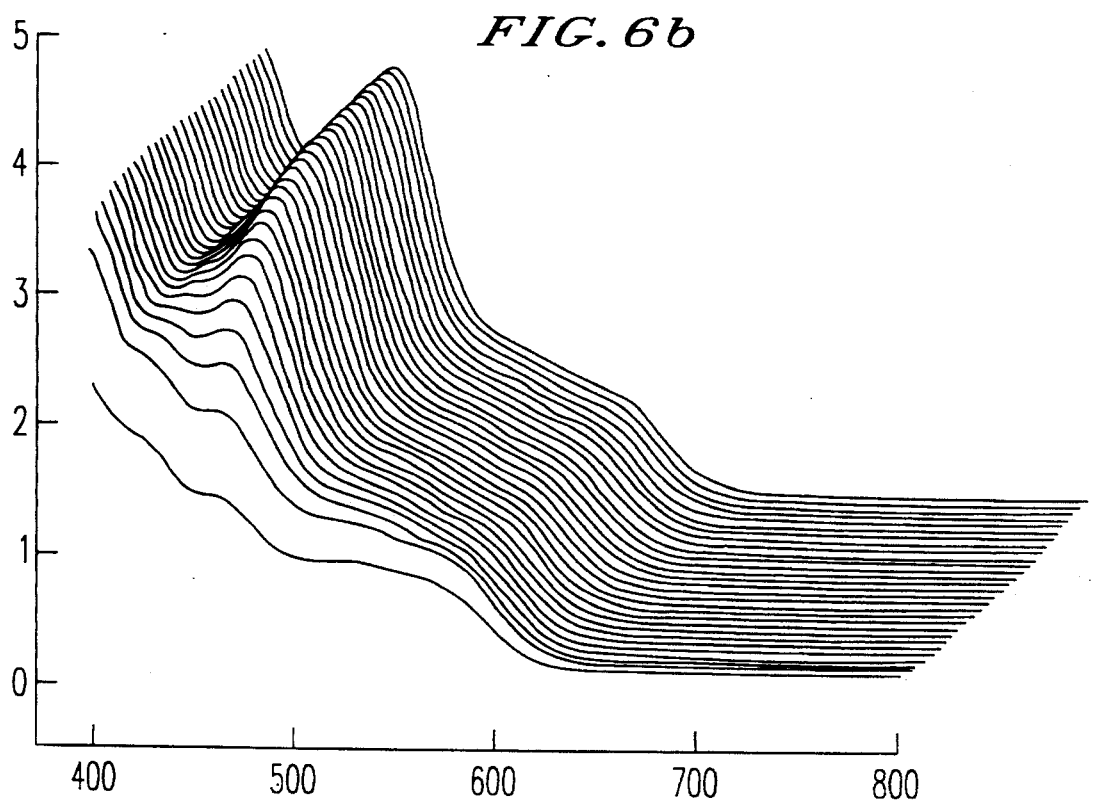
Figure 6C:
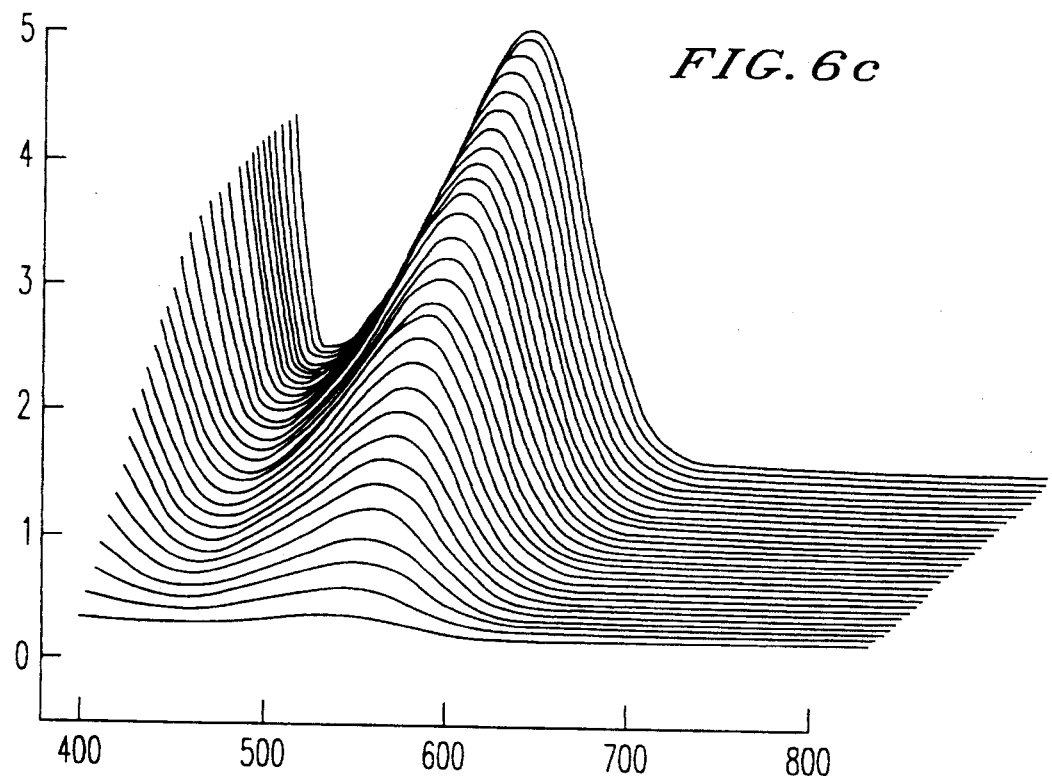
Figure 7A:
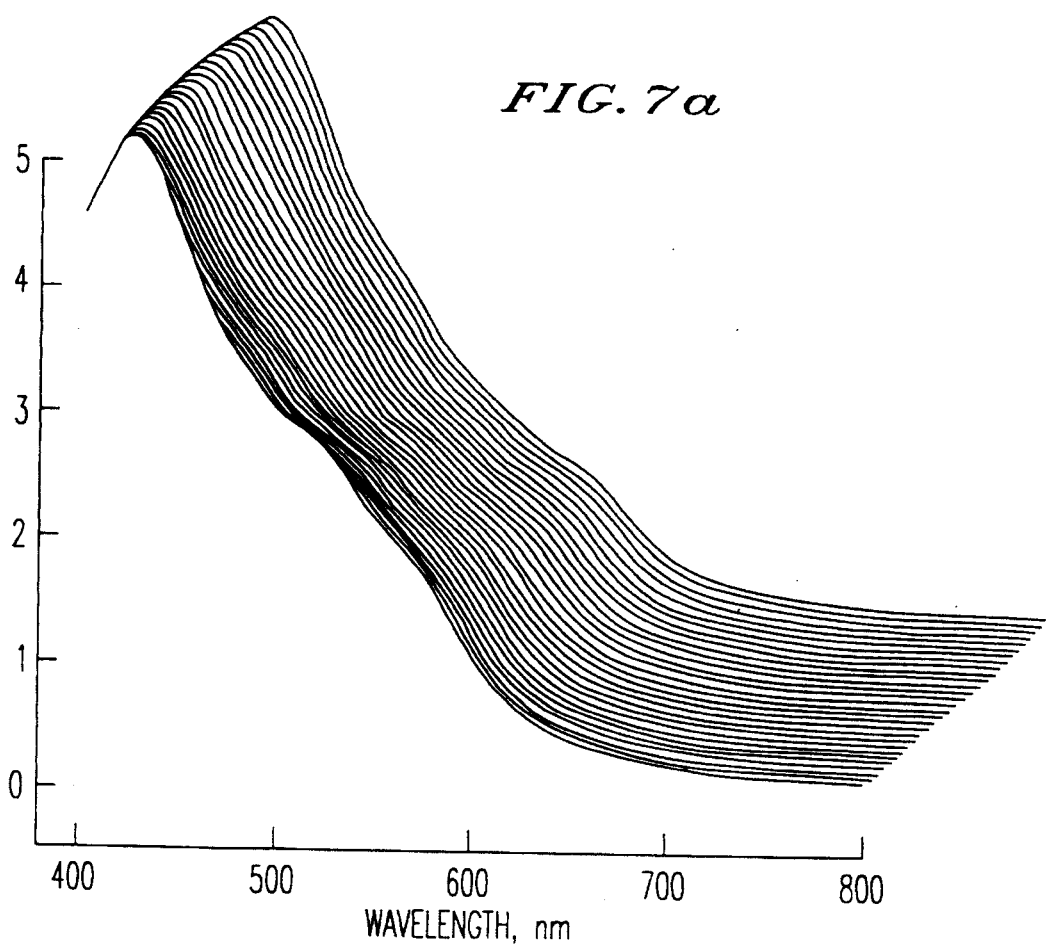
Figure 7B:
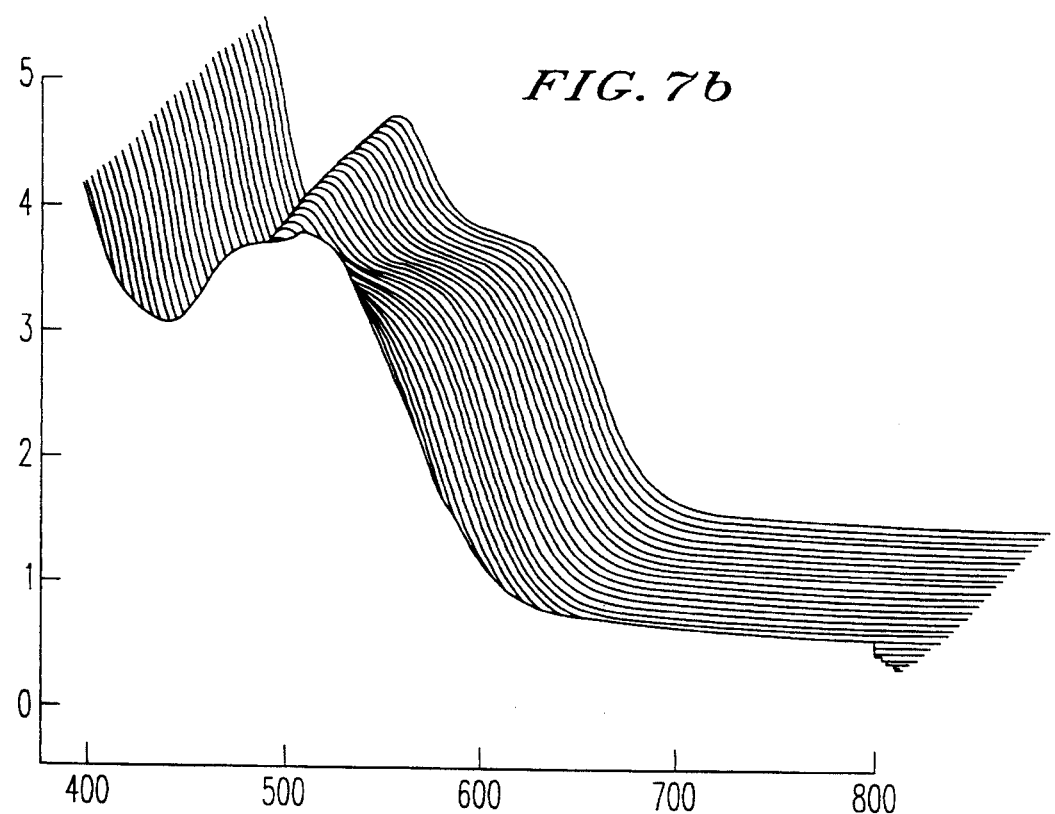
Figure 7C:
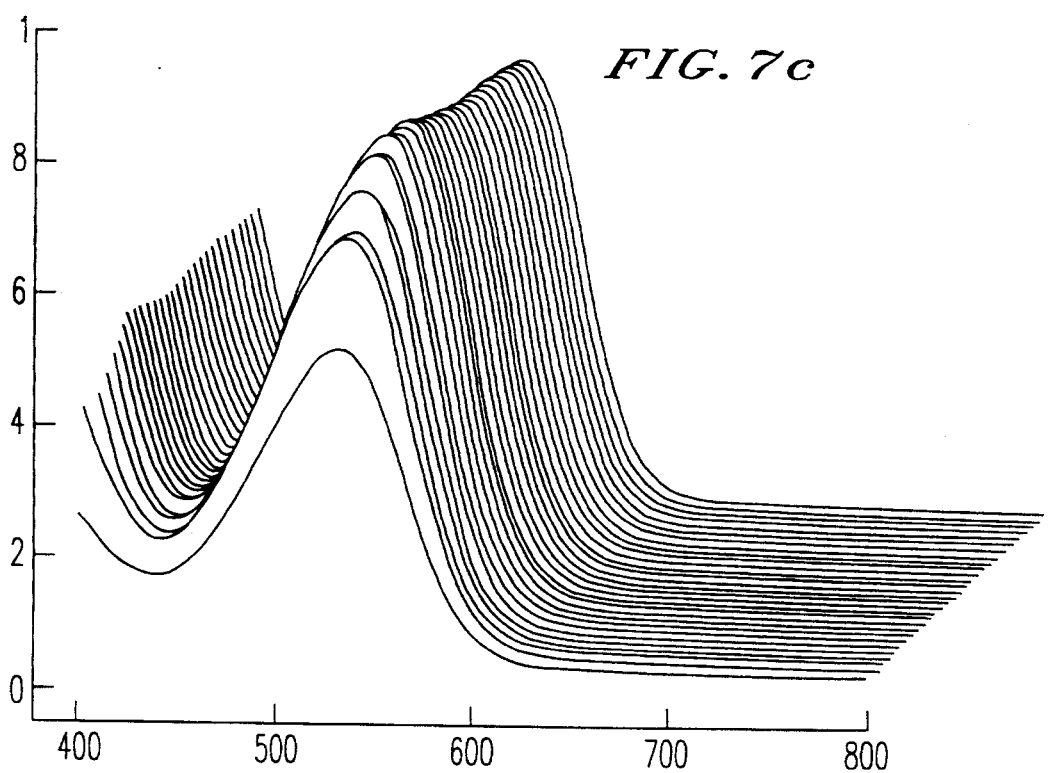
Figure 8A:
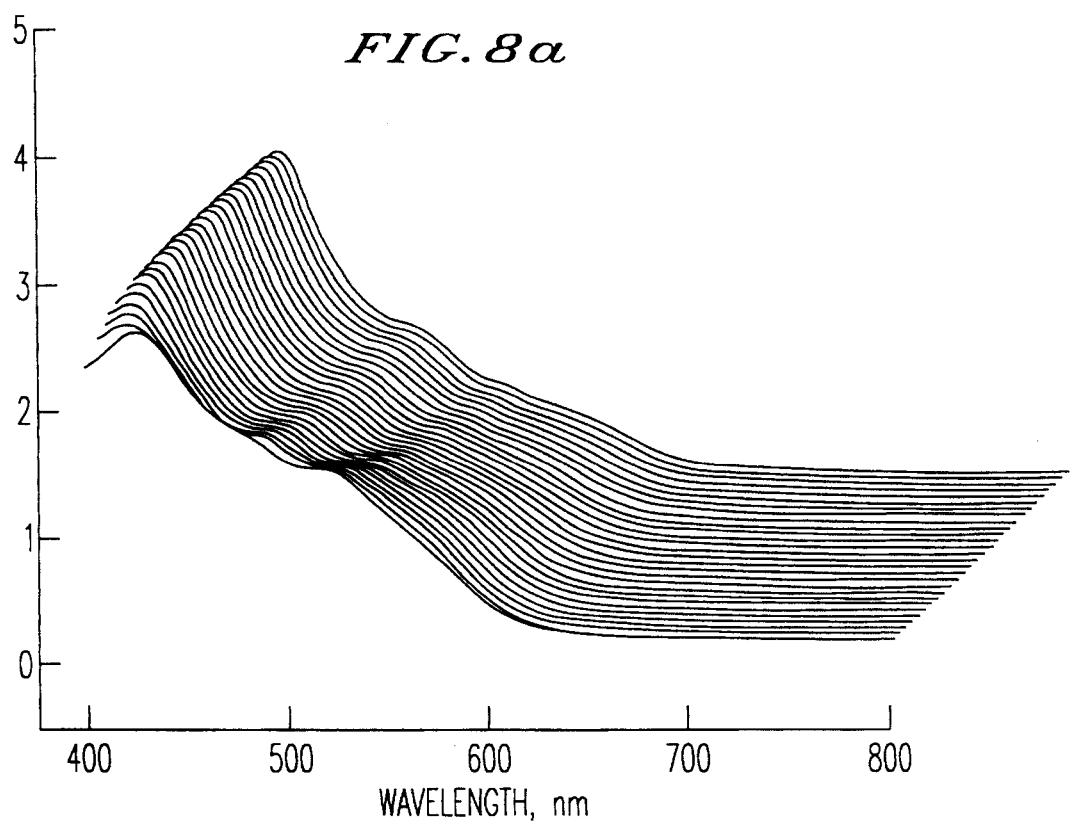
Figure 8B:
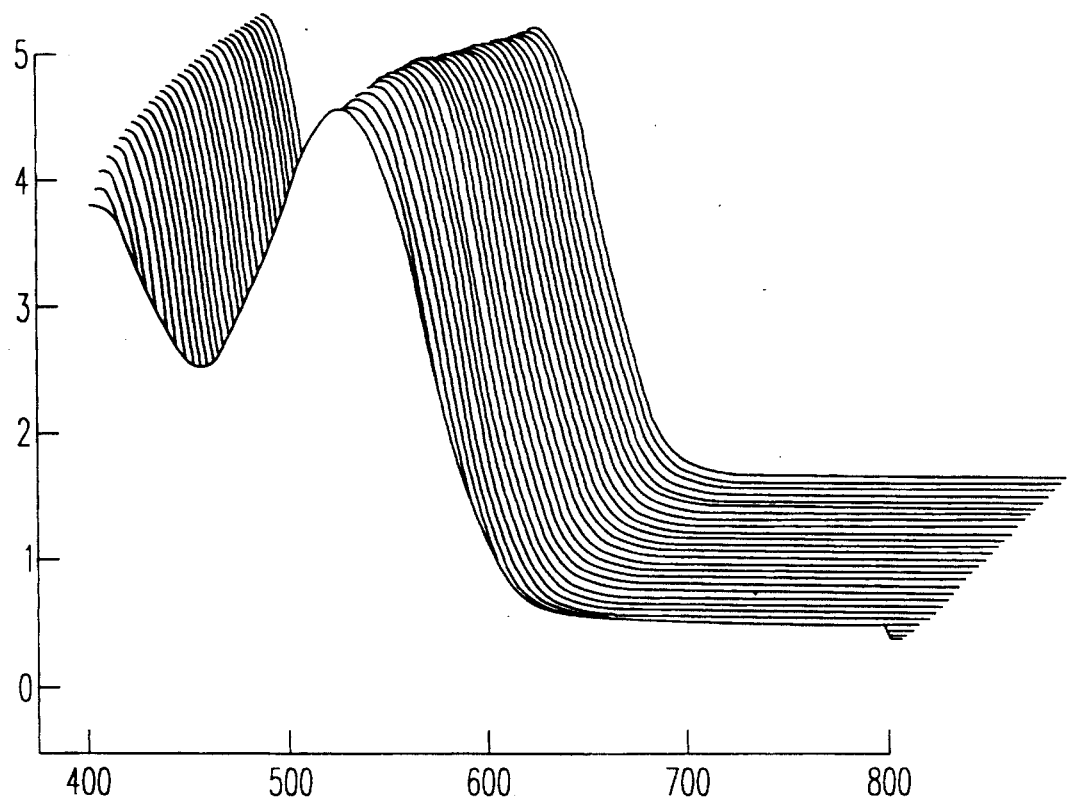
Figure 8C:
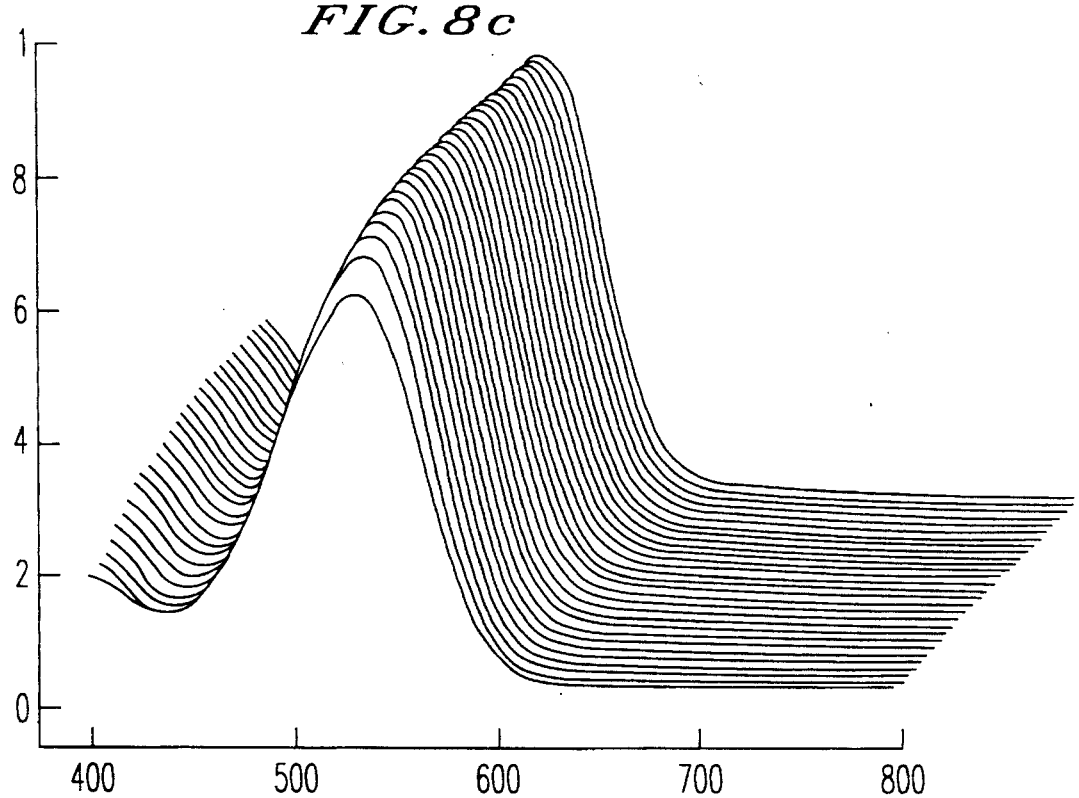
Figure 9A:
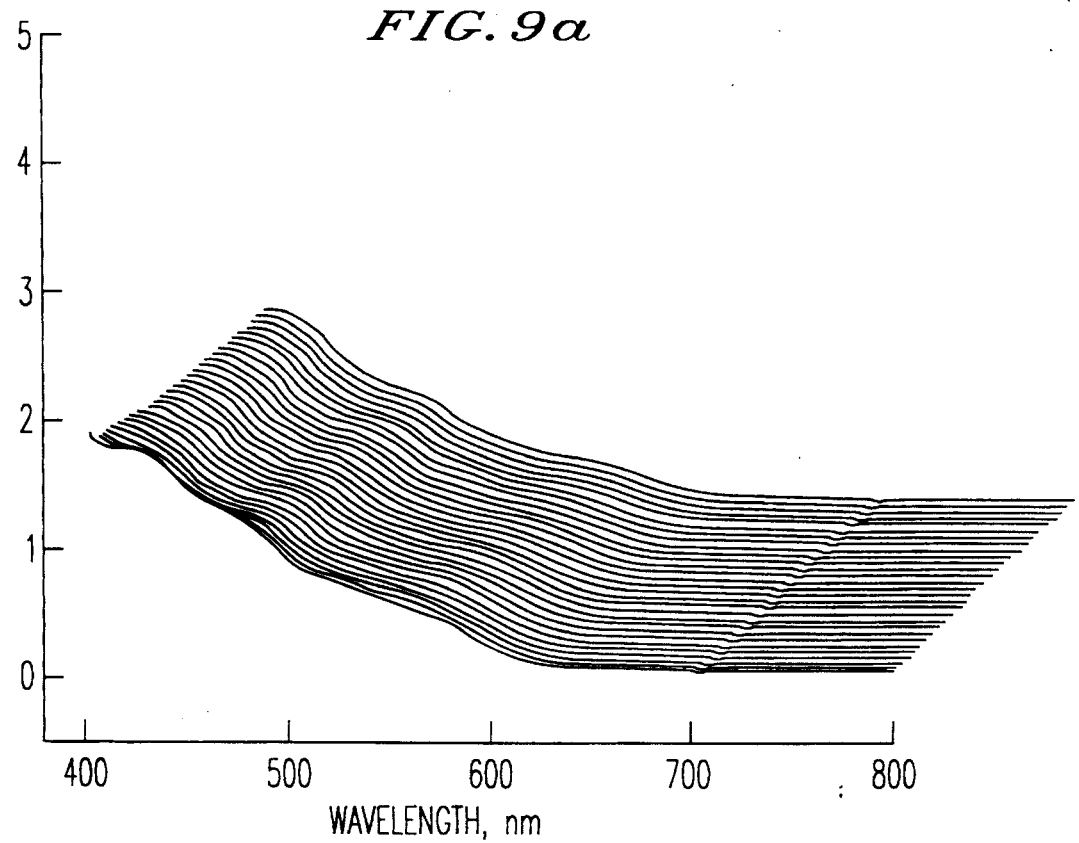
Figure 9B:
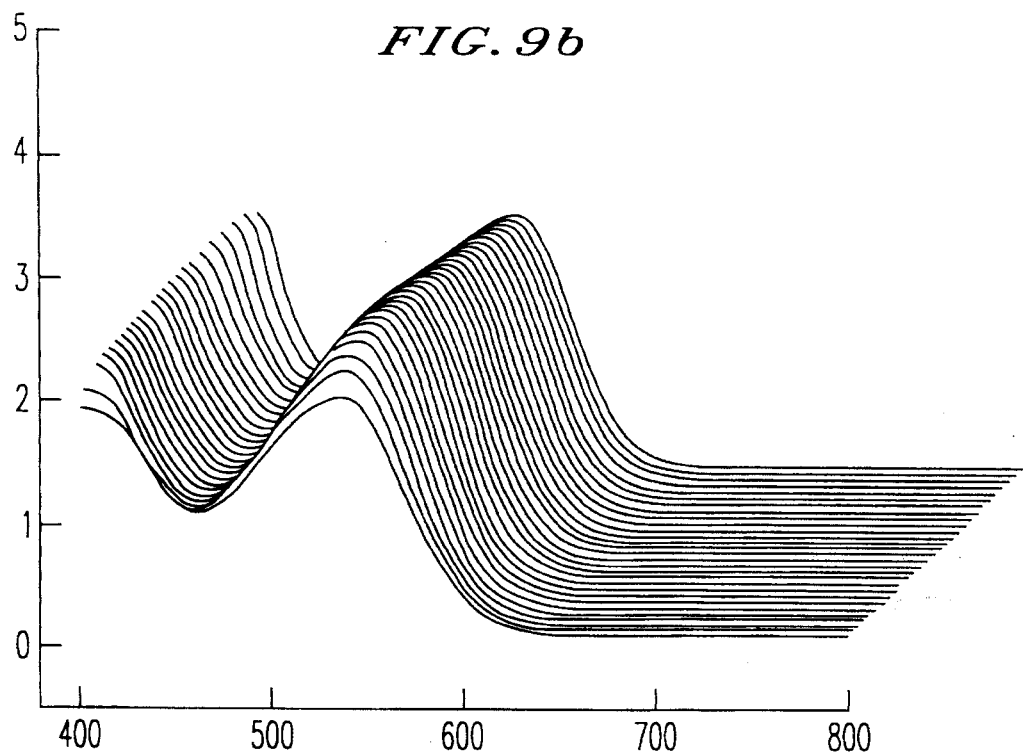
Figure 9C:
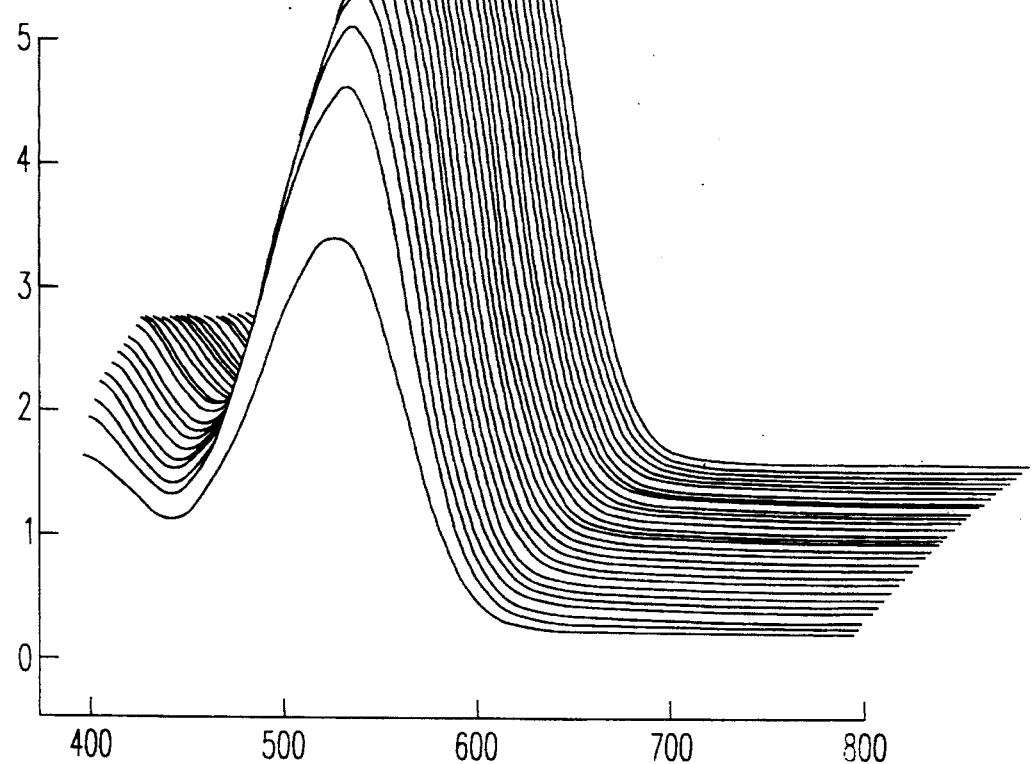

The concentration of the base has also been found to influence the assay sensitivity. FIGS. 4 and 5 illustrate how the water and base concentrations in the Fujiwara reaction, respectively, can be manipulated to modify the sensitivity of the reaction and the recognition of the four trihalomethanes. In a most preferred embodiment of this TTHM assay, the normalization of the THM response has been accomplished in the present invention by using a pyridine reagent containing approximately 16%±1% of water, a 1.5±0.2 min boiling step (i.e. which eliminates the recognition of trichloroethylene), and a soluble organic ammonium hydroxide base, such as tetrabutylammonium hydroxide, at a concentration of approximately 0.1%±0.025%.

The direct analysis of trihalomethanes in water by the present single phase method is more sensitive than the classical, two-phase Fujiwara method by approximately two orders of magnitude, and the sensitivity (on a weight basis) to individual THMs in the present method has been normalized to provide approximately equivalent detection of each THM, whereas the conventional Fujiwara reaction has a factor of 4 difference between the various THM reaction products.

As an example of how the absorbance spectra of the Fujiwara products changes dependant on the amount of water present in the reaction, FIGS. 6–9 show the progressive change in the spectra of chloroform, bromodichloromethane, chlorodibromomethane and bromoform, respectively, when the water concentration is changed from 0% (FIGS. 6–9(a)) to 5% (FIGS. 6–9(b)) and up to 12.5% (FIGS. 6–9(c)). These spectra show that at different concentrations of water, the THMs form different Fujiwara products at different rates. This provides the characteristic absorbance "fingerprint" for each of the THMs. However when the water concentration is sufficiently high, preferably 16% by volume, each of the THMs forms the same Fujiwara reaction product, thus allowing for normalization of the response for the THMs.

In an additional embodiment of the present invention, a kit is provided for performing the TTHM assay described above. The kit contains the following: (1) an SPE sample collection means, (2) an elution solvent system, (3) a plurality of assay vessels and (4) a means for measuring sample absorbance. Suitable SPE sample collection means have been described above and include a GAC impregnated filter in a plastic housing containing two connection tube connecting fittings (e.g. luer lock), an in-line mini-GAC column similarly configured to contain fittings or a cylindrical column equipped with fittings capable of coupling to a pressurized water source, as described above.

The elution solvent system includes a solvent capable of essentially quantitative removal of the adsorbed THMs from the SPE material, which solvent is also compatible with the Fujiwara reaction, wherein the solvent is contained in a suitable container. Preferably the solvent is pyridine. In addition to the solvent, the elution solvent system can optionally contain a base reagent or water or both. If the system contains a base reagent, the preferred base is tetrabutyl ammonium hydroxide (TBAH) in an amount of 0.1%, relative to the weight of solvent. If the system contains water, the amount of water contained is preferably kept to a minimum in order to allow several different concentrations to be used in the Fujiwara reaction of the assay, while maintaining a maximum water concentration of 12.5% by volume in the reaction.

When either or both of the base and water are not present in the elution solvent system, the kit further comprises one or more containers having therein a base reagent in a small (<1 mL) amount of solvent (preferably the same solvent used in the elution step) or water in an amount sufficient to provide the desired percentage of water in each of the plurality of Fujiwara reactions performed in the assay. The containers used for the solvent elution system and/or the additional base reagent and water, if needed, are any conventional container which is compatible with the various chemical species used in the assay. Suitable containers can be prepared from materials such as glass, polypropylene, polyethylene, or polyester.

The plurality of assay vessels can be prepared from any of the same materials used in the preparation of the containers for the solvent elution system, as long as the vessels are chemically compatible with the reagents and conditions used in the Fujiwara reaction. Preferably, the kit contains from 2 to 4 assay vessels, per assay to be performed.

The means for measuring sample absorbance after the Fujiwara reaction comprises a photometer to measure the actual absorbance of the samples in the assay vials and a calibration curve from which one can arrive at the concentration of total THMs in the sample based on the measured absorbance. As a suitable photometer, any photometer capable of measuring absorbance in the range from 350 to 600 nm is acceptable, with photometers capable of measuring absorbance at 538–540 nm being preferred. The calibration curve can be readily prepared by performing the method of the present invention using standard samples containing known amounts of THMs.

In a preferred embodiment of the kit, the kit further comprises a heating bath and a cooling bath. These baths can be filled with water, or another suitable heat transfer medium. The heating bath is used for heating the Fujiwara reaction at a desired temperature for a desired time, preferably at 100° C. for from 0.5 to 10 min, most preferably for 1.5 min. Upon the completion of the heating step, the reaction vessel containing the reaction mixture is transferred to a cooling bath which has sufficient cooling capability to cool the sample from 100° C. to room temperature in a very short period of time, preferably within 1.5 to 2.5 minutes, most preferably in 2 minutes.

Other features of the present invention will become apparent in the course of the following description of specific examples which are provided herein for illustrative purposes only and are not intended to limit the present invention unless otherwise specified.

EXAMPLES

Extraction of TCE and THMs from aqueous solution

The following table illustrates the removal of THMs and TCE from an aqueous influent source with spiked approximately ppb of each analyte, when pumped through a 25 cm diameter EMPORE (3M Corp.) GAC filter at 100 mL/min. The concentrations of TCE and THMs were measured by purge and trap GC (EPA Method 502.1).

| Volume effluent pumped through filter | TCE (ppb) | $CHCl_3$ (ppb) | $CHBrCl_2$ (ppb) | $CHBr_2Cl$ (ppb) | $CHBr_3$ (ppb) |
|---|---|---|---|---|---|
| OmL (Blank) | 0.19 | 0.43 | 0.0 | 0.0 | 0.0 |
| 50 | 0.0 | 0.34 | 0.0 | 0.0 | 0.0 |
| 250 | 0.0 | 0.10 | 0.0 | 0.0 | 0.0 |

| Volume effluent pumped through filter | TCE (ppb) | CHCl₃ (ppb) | CHBrCl₂ (ppb) | CHBr₂Cl (ppb) | CHBr₃ (ppb) |
|---|---|---|---|---|---|
| 500 | 0.0 | 0.28 | 0.0 | 0.0 | 0.0 |
| 750 | 0.0 | 0.88 | 0.20 | 0.0 | 0.0 |
| 1000 | 0.0 | 2.33 | 0.12 | 0.0 | 0.0 |
| Influent Water (prefilter) | 11.4 | 11.7 | 8.79 | 9.53 | 9.25 |

Further studies with TCE showed that the extraction efficiency can be independent of the flow rate of a spiked water sample through the GAC filter.

| | [TCE] (by GC) | |
|---|---|---|
| Flow Rate | Influent Water | Effluent Water |
| 10 mL/min | 12.5 ppb | 0.1 ppb |
| 25 | 22.4 | 0.2 |
| 50 | 17.7 | <0.1 |
| 100 | 19.5 | 0.1 |
| 200 | 11.7 | 0.1 |

These results show the flow independent ability of the SPE material (in this case a GAC filter) to efficiently and nearly quantitatively extract the TCE and THMs from an extremely dilute solution.

TTHM Procedure

A sample to be tested for THM concentration is collected in a sample container which holds at least twice the volume of sample to be pumped through the GAC extraction column. The sample container is then connected to the GAC extraction column via inert tubing, such as VITON, and the tubing is also connected to a peristaltic pump. Prior to connecting the sample container to the GAC extraction column, the GAC extraction column is preconditioned by charging the column with approximately 5–10 mL of methanol using a syringe. The peristaltic pump is then used to pump the sample from the sample container through the GAC extraction column at a rate of about 100 mL/min (although higher or lower rates can be used) to cause the THMs to be adsorbed by the GAC column. After half of the sample has been pumped from the sample container through the GAC extraction column, the GAC column is removed from the tubing and a syringe containing pyridine is attached thereto. The pyridine is pumped by syringe, slowly through the column into a reaction vessel, causing elution of the adsorbed THM compounds from the GAC column.

To the resulting pyridine solution in the reaction vessel, is added a solution of concentrated tetrabutylammonium hydroxide (TBAH) so that the final concentration of TBAH is 0.1%. Depending on the amount of water present in the sample after elution from the GAC column, water can be added to bring the final water concentration up to 16%. The reaction vessel is then capped and vigorously mixed for 3–5 sec. Concurrently, a standard sample containing a known amount of THMs is put through the same pyridine, TBAH, water reaction in a separated reaction vessel.

Both the sample and the standard are then placed into a boiling water bath and incubated for 90 sec. When boiling the sample and standard the portion of the reaction vessel containing the reaction mixture should be completely immersed in the water bath. After boiling, the sample and standard are transferred to a water bath at 25° C. and allowed to stand for 2 min. The sample and standard are then removed from the bath and the absorbance of each is measured at 540 nm versus a blank containing only water.

From the resulting As40 for the sample, the concentration of the THMs can be determined when compared to a standard curve.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. A method for the selective, sensitive detection of total trihalomethanes (TTHM), in an aqueous sample comprising:

a) contacting said aqueous sample with a solid phase extraction medium to essentially quantitatively adsorb trihalomethanes (THMs) from said aqueous sample;

b) eluting the adsorbed THMs from said solid phase extraction medium with pyridine to essentially quantitatively remove THMs from the solid phase extraction medium;

c) contacting the thus formed pyridine solution of eluted THMs with 0.1±0.025% of a base reagent and from 14–18% by volume of water to form a chromophoric product, wherein said amounts of base and water are sufficient to provide an optical absorption response for each chromophoric product which is approximately equal on a weight/weight basis to an optical absorption response for each of the other chromophoric products; and d) determining concentration of TTHM by measuring an absorbance for the product of step c) and comparing said absorbance to a standard calibration curve.

2. The method of claim 1, wherein said amount of water is 16% by volume.

3. The method of claim 1, wherein said solid phase extraction medium is a granular activated carbon.

4. The method of claim 1, wherein step c) further comprises heating the mixture of step c) at 100° C. for a time of from 0.5 min. to 10 min.

5. The method of claim 4, wherein said heating is performed for a time of 1.5 min.

6. The method of claim 1, wherein said base reagent is a member selected from the group consisting of tetra $C_1$–$C_7$ alkyl ammonium hydroxides and $C_7$–$C_{10}$ aralkyl-tri-$C_1$–$C_7$-alkyl ammonium hydroxides.

7. The method of claim 6, wherein said base reagent is trimethyl benzyl ammonium hydroxide.

8. The method of claim 6, wherein said base reagent is tetrabutylammonium hydroxide.

9. The method of claim 4, wherein said base reagent is present in an mount of 0.1% by weight.

10. A kit for use in performing a total trihalomethane (TTHM) assay, comprising:

a solid phase extraction (SPE) sample collection means sufficient to provide essentially quantitative adsorption of trihalomethanes (THMs) from an aqueous sample;

an elution solvent system in a suitable container and capable of essentially quantitative elution of THMs adsorbed on an SPE material used in said SPE sample collection means and wherein said elution solvent system is compatible with conditions under which a Fujiwara reaction is performed, wherein said elution solvent system comprises from 0.1±0.025% by weight of a base reagent and from 14–18% by volume of water;

a plurality of assay vessels; and a means for measuring sample absorbance.

11. The kit of claim 10, wherein said elution solvent system further comprises pyridine.

12. The kit of claim 10, wherein said base reagent is tetrabutylammonium hydroxide.

13. The kit of claim 10, wherein said means for measuring sample absorbance comprises a photometer which measures sample absorbance at 538–540 nm and a sample calibration curve correllating sample absorbance at 538–540 nm after 10 min of reaction with the total THM concentration in the sample.

14. The kit of claim 10, further comprising a heating bath and a cooling bath, wherein said heating bath is capable of maintaining a reaction temperature of 100° C. for a period of time of from 0.5 to 10 min and wherein said cooling bath is capable of cooling a reaction mixture from 100° C. to room temperature in a period of time of 1.5–2.5 min.

15. The kit of claim 10, wherein said SPE material is a granular activated carbon.

* * * * *